United States Patent
Reiter et al.

(10) Patent No.: US 6,908,999 B2
(45) Date of Patent: Jun. 21, 2005

(54) PROCESS FOR THE PREPARATION OF {2-[4-α-PHENYL-P-CHLOROBENZYL) PIPERAZIN-1-YL]ETHOXY} ACETIC ACID AND NOVEL INTERMEDIATES THEREFOR

(75) Inventors: Jozsef Reiter, Budapest (HU); Peter Trinka, Budapest (HU); Ferenc Bartha, Tiszavasvari (HU); Gyula Simig, Budapest (HU); Kalman Nagy, Budapest (HU); Györgyi Vereczkeyne Donath, Budapest (HU); Norbert Nemeth, Sopron (HU); György Clementis, Budapest (HU); Peter Tömpe, Budapest (HU); Pal Vago, Budapest (HU)

(73) Assignee: Egis Gyogyszergyar Rt., Budapest (HU)

( * ) Notice: Subject to any disclaimer, the term of this patent is extended or adjusted under 35 U.S.C. 154(b) by 107 days.

(21) Appl. No.: 10/148,704
(22) PCT Filed: Nov. 29, 2000
(86) PCT No.: PCT/HU00/00123
§ 371 (c)(1), (2), (4) Date: Jul. 3, 2002
(87) PCT Pub. No.: WO01/40211
PCT Pub. Date: Jun. 7, 2001

(65) Prior Publication Data
US 2003/0092911 A1 May 15, 2003

(30) Foreign Application Priority Data
Nov. 30, 1999 (HU) .............................................. 9904438
Nov. 30, 1999 (HU) .............................................. 9904439

(51) Int. Cl.$^7$ ............................................. C07D 295/14
(52) U.S. Cl. ....................................................... 544/396
(58) Field of Search .......................................... 544/396

(56) References Cited

U.S. PATENT DOCUMENTS

| | | | | | |
|---|---|---|---|---|---|
| 4,525,358 | A | * | 6/1985 | Baltes et al. | 514/255.04 |
| 5,347,060 | A | * | 9/1994 | Hellring et al. | 570/235 |
| 6,046,332 | A | * | 4/2000 | Tao et al. | 544/396 |
| 6,140,501 | A | * | 10/2000 | Duchene et al. | 544/386 |

FOREIGN PATENT DOCUMENTS

| EP | 0 058 146 | 8/1982 |
|---|---|---|
| WO | WO-97/37982 | 10/1997 |

OTHER PUBLICATIONS

Advanced Organic Chemistry (2$^{nd}$. Ed.) by Jerry March, p. 353 (1977).*
A Novel Synthesis of the Enantiomers of an Antihystamine Drug . . . by Opalka et al (SYNTHESIS vol. 7 1995).

* cited by examiner

Primary Examiner—Emily Bernhardt
(74) Attorney, Agent, or Firm—Herbert Dubno; Jonathan Myers

(57) ABSTRACT

The invention refers to a novel process for the preparation of {2-[-(α-phenyl-p-chlorobenzyl)piperazin-1-yl]ethoxy}acetic acid, which comprises hydrolyzing an N,N-disubstituted {2-[-(α-phenyl-p-chlorobenzyl)piperazin-1-yl]ethoxy}acetamide, wherein said substituents are selected from alkyl groups having 1 to 4 carbon atoms optionally substituted by a phenyl group, alkenyl groups having 2 to 4 carbon atoms or cyclohexyl groups, or the substituents together with the adjacent nitrogen atom of the acetoamido group, form a morpholino group.

3 Claims, No Drawings

PROCESS FOR THE PREPARATION OF {2-[4-α-PHENYL-P-CHLOROBENZYL) PIPERAZIN-1-YL]ETHOXY} ACETIC ACID AND NOVEL INTERMEDIATES THEREFOR

FIELD OF THE INVENTION

The invention refers to a novel process for the preparation of {2-[4-(α-phenyl-p-chlorobenzyl)piperazin-1-yl]ethoxy}acetic acid of the formula

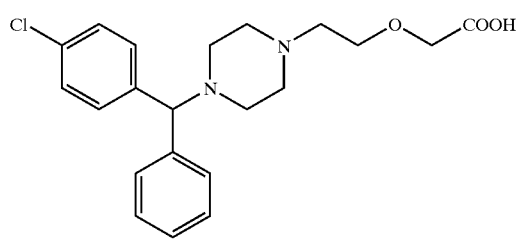

I

{2-[4-(α-Phenyl-p-chlorobenzyl)piperazin-1-yl]ethoxy}acetic acid is known under the international non-proprietary name cetirizine that is widely used as the ingredient of antiallergic pharmaceutical compositions.

The invention also refers to novel {2-[4-(α-phenyl-p-chloro-benzyl)piperazin-1-yl]ethoxy}acetamides of the formula

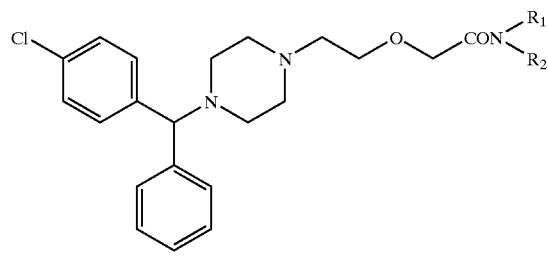

II wherein $R_1$ and $R_2$ represent, independently, a $C_{1-4}$ alkyl group optionally substituted by a phenyl group, a $C_{2-4}$ alkenyl group or a cyclohexyl group, or $R_1$ and $R_2$ form together with the adjacent nitrogen atom a morpholino group, and acid addition salts thereof which are useful intermediates in the synthesis of cetirizine.

BACKGROUND OF THE INVENTION

Several methods are known for the preparation of cetirizine of the formula I. According to European Patent Application No. 58,146 (Chem. Abstr., 98, 34599r), an ester or an amide of the formula

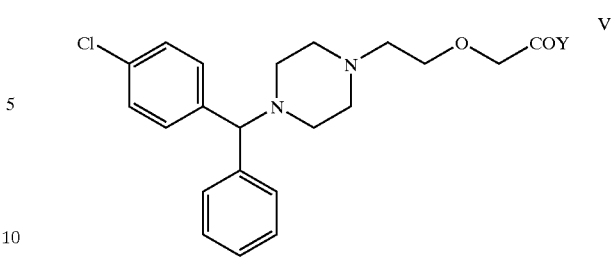

V wherein Y stands for a group of the formula —$OR^1$ or an amino group, wherein $R^1$ means an alkyl group, is hydrolized to obtain the compound of the formula I.

Starting from the methyl ester of the formula V, after hydrolysis with potassium hydroxide, the potassium salt of cetirizine is obtained in a yield of 59%. From the potassium salt the corresponding acid is formed in a yield of 81%, and the desired dihydrochloride of cetirizine is obtained in a yield of 80%. Thus, the total yield of the known process amounts to 38.2%. A rather great drawback of the known process consists in the fact that the esters of the formula V used as the starting compound can be prepared only with difficulties and in a poor yield. Thus, the 1-[(4-chloro-phenyl)phenylmethyl]piperazine of the formula

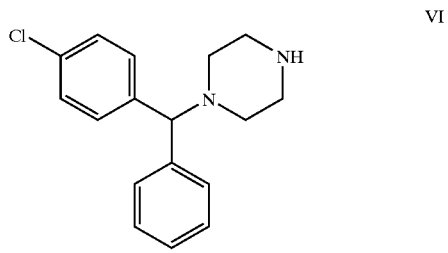

VI is reacted with methyl 2-chloroethoxyacetate of the formula

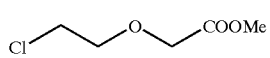

VII to obtain the corresponding methyl ester of the formula V—after chromatography—in a yield of as low as 10.6%.

In the European Patent Application referred to above the possibility is mentioned that cetirizine can be prepared also from the acetic amide of the formula V, wherein Y stands for an amino group, by hydrolysis. However, neither any Example, nor yield data are given for the hydrolysis of the acetic amide of the formula V. According to a later communication (Synthesis, 1995, 766), the acetamide of the formula V is hydrolized in hydrochloric acid at 50° C. to obtain cetirizine in a yield of 71%.

Even three methods are known for the preparation of the acetamide of the formula V. For example, the 1-[(4-chloro-phenyl)phenylmethyl]-piperazine of the formula VI is reacted with 2-chloroethoxy-acetamide of the formula

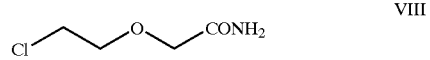

VIII in the presence of an acid binding agent to obtain the acetamide of the formula V in a yield of 47%. According to a second method, the {2-[4-(α-phenyl-p-chlorobenzyl) piperazin-1-yl]}ethanol of the formula

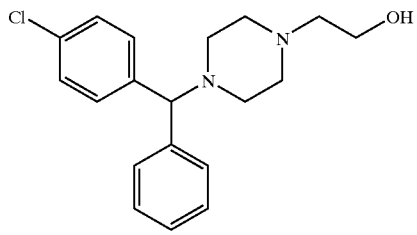

is converted to the sodium salt with sodium hydride, and the salt is reacted with a chloroacetamide of the formula

wherein X represents a chloro atom, $R_1$ and $R_2$ stand for a hydrogen atom. However, the yield of the reaction is merely 11%. According to the third method, the acetamide of the formula V can be also prepared from the corresponding methyl ester of the formula V, wherein Y means a methoxy group, by reaction with ammonia in a yield of 54%. Taking into consideration the low yield (27.8%) of the preparation of the methyl ester, the total yield is as low as 15.0%. Consequently, the latter known synthesis of cetirizine is uneconomical, too.

The process of UK-P No. 2 225 320 (Chem. Abstr., 113, 191395s) aims at the elimination of the disadvantages of the above known processes by preparing cetirizine from the {2-[4-(α-phenyl-p-chlorobenzyl)piperazin-1-yl]}ethanol of the formula III which is converted to the potassium salt with potassium tert-butylate. The potassium salt is reacted with sodium chloro-acetate to obtain cetirizine dihydrochloride in a yield of 48.8%. In addition, 5.1% of a second generation product are obtained. Also an improved process is described for the preparation of the {2-[4-(α-phenyl-p-chlorobenzyl) piperazin-1-yl]}ethanol of the formula III according to which 1-[(4-chlorophenyl)phenyl-methyl]piperazine of the formula VI is reacted with ethylene chlorohydrine in a yield of 90.4%, the total yield of the synthesis, referred to the piperazine derivative of the formula VI, is merely 48.7%.

The latter known process has a further drawback. The reaction of the ethanol derivative of the formula III with sodium chloro-acetate can be carried out in a relatively acceptable yield if the reactants are added in several portions to the solution of the ethanol derivative of the formula III. The addition of the reactants is to be programmed on the basis of a continuous monitoring of the composition of the reaction mixture. This technology is rather awkward, especially on industrial scale.

The latter known process is tried to be improved by the method described in PL-P No. 163 415 (Chem. Abstr., 123, 55923s) according to which the reaction is performed in a system consisting of two phases, in the presence of an indifferent organic solvent and aqueous sodium hydroxide solution to obtain cetirizine dihydrochloride in a yield of 60%. Although this method is less complicated than the one known from UK-P No. 2 225 320, the total yield amounts to only 54% as calculated for the ethanol derivative of the formula III that can be prepared in the most favourable way.

A further method for the preparation of cetirizine is known from UK-P No. 2 225 321 (Chem. Abstr., 113, 191396t) according to which the the 1-[(4-chloro-phenyl) phenylmethyl]-piperazine of the formula VI is reacted with chloroethoxyacetonitrile to obtain the nitrile derivative of the formula

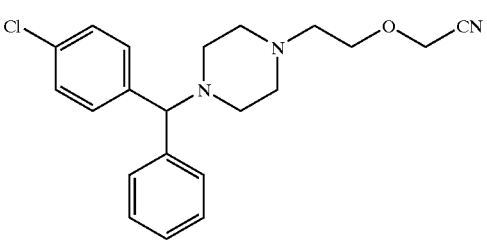

that is hydrolized in acidic or alkaline medium to cetirizin. In this way, cetirizin dihydrochloride is obtained from the nitrile derivative of the formula IX in a total yield of 60.5% in case of the acidic hydrolysis, and in a total yield of 65.6% in case of the alkaline hydrolysis.

However, the reaction of 1-[(4-chlorophenyl) phenylmethyl]-piperazine of the formula VI with chloroethoxyacetonitrile produces the nitrile derivative in a yield of 86.4% thereby reducing the total yield of the synthesis to 52.2% and 56.6%, respectively.

It should be also taken into consideration that, according to the literature [E. J. Salmi, R. Leimu and H. Kallio, Suomen Kemistilehti, 17B, 17–19 (1944)], chloroethoxyacetonitrile can be prepared from ethylene chlorohydrin in two steps using the very poisonous copper(l) cyanide in a total yield of 58%.

Finally, a simple method of preparation is aimed by the process known from published European Patent Application No. 801,064 according to which cetirizine is prepared from 1-[(4-chlorophenyl)phenylmethyl]-piperazine of the formula VI with 2-chloroethoxyacetic acid in an indifferent solvent in the presence of an acid binding agent. The publication has only one example that does not contain either yield or quality data for the product. Furthermore, a great drawback of this method consists in the unavailability of 2-chloroethoxyacetic acid on an industrial scale.

The aim of the invention is to provide an economical process for the preparation of cetirizine that satisfies the most severe quality requirements.

SUMMARY OF THE INVENTION

It has been found that the above aim is achieved if, in the process for the preparation of {2-[4-(α-phenyl-p-chlorobenzyl)piperazin-1-yl]ethoxy}acetic acid of the formula I or a pharmaceutically suitable acid addition salt or metal salt thereof through hydrolyzing a corresponding acetamide in alkaline or acidic medium, and, if desired, converting the product formed to an acid addition salt or metal salt and/or liberating the base from the acid addition salt or metal salt, a compound of the formula II or an acid addition salt thereof is used as the acetamide, and, if desired, the hydrolysis is carried out in the presence of a phase transfer catalyst.

The invention includes the {2-[4-(α-phenyl-p-chlorobenzyl)-piperazin-1-yl]ethoxy)-acetamides of the formula II that are novel compounds.

DESCRIPTION OF THE PREFERRED EMBODIMENTS

In the process of the invention, the starting compound is an acetamide of the formula II or an acid addition salt thereof formed with an inorganic or an organic acid, and the starting compound is subjected to alkaline or acidic hydrolysis in a manner known per se, if, desired, in the presence of a phase transfer catalyst.

If desired, the product formed is converted to a pharmaceutically suitable acid addition salt or metal salt and/or the base is liberated from the acid addition salt or metal salt thereof in a manner known per se.

The hydrolysis of the {2-[4-(α-phenyl-p-chlorobenzyl)piperazin-1-yl]ethoxy}-acetamides of the formula II takes place surprisingly fast and completely, without the formation of by-products, in 1–8 hours depending on the character of $R_1$ and $R_2$. From the reaction mixture, cetirizine or the dihydrochloride thereof can be simply separated in a very pure form that satisfies the extremely severe HPLC quality requirements of European Pharmacopoeia, 3, (1997) at 1084.

For the expert it is surprising that the hydrolysis of the {2-[4-(α-phenyl-p-chlorobenzyl)piperazin-1-yl]ethoxy}-acetamides of the formula II proceeds so fast since it is known from the literature that dialkyl acetamides are stable compounds, the hydrolysis of which takes place slowly and requires strong reaction conditions. For example, N,N,N',N'-tetraethyl-5,5-dimethyl-3,7-dioxanone diamide was hydrolized in 3 N aqueous sodium hydroxide under boiling for 5 days to obtain the corresponding dicarboxylic acid in a yield of 91.5% [J. Chem. Soc. Perkin Trans. I., 1981, 741–745, Chem. Abstr., 95, 42286q (1981)]. However, after boiling for 5 days, only 39.8% of the corresponding N,N,N',N'-tetramethyl derivative was converted to the corresponding dicarboxylic acid that was separated as the methyl ester. Moreover, when, for example, the threo-10,11-dihydroxy-N,N-dimethyl-nonadecaneamide was boiled in ethanol with 2 N aqueous sodium hydroxide solution for 1 hour, no decomposition was experienced to form the corresponding carboxylic acid [J. Chem. Soc., 1961, 351–356, Chem. Abstr., 55, 12276g (1961)]. This is the cause of the practice according to which carboxylic amides are hydrolized to carboxylic acid with a concentrated alkali or rather in a concentrated acidic medium in the presence of nitrites [Houben-Weyl: Methoden der Organischen Chemie, Vol. 8, 432; A. R. Katritzky et al., Comprehensive Organic Functional Group Transformations, Vol. 5, 34–36 (1995)].

Preferably, N,N-dimethyl-{2-[4-(α-phenyl-p-chlorobenzyl)-piperazin-1-yl]-ethoxy}acetamide is used as the acetamide of the formula II.

According to a preferred method of the invention, the hydrolysis of the {2-[4-(α-phenyl-p-chlorobenzyl)piperazin-1-yl]ethoxy}-acetamides of the formula II is carried out in an aqueous solution of an alkali metal hydroxide, preferably sodium or potassium hydroxide, wherein the concentration of the alkali in the solution amounts to 2–25% by mass, preferably 6–16% by mass, suitably about 12% by mass, generally at 40–110° C., preferably at 70–110° C., suitably at the boiling point of the solution. After the alkaline hydrolysis, the product is separated as follows: the reaction mixture is diluted with water, acidified with hydrochloric acid to a pH value of 3.8–4.0, the cetirizin base is dissolved in an organic solvent being immiscible with water, preferably dichloromethane, the organic solution is evaporated to dryness under reduced pressure, and the remaining honey-like residue is dissolved in 5–36%, preferably 10–20%, suitably about 16% hydrochloric acid. Then, a water-miscible organic solvent, preferably acetone, methyl ethyl ketone or tetrahydrofuran is added to the solution to crystallize the dihydrochloride, or the hydrochloric acidic solution is concentrated under reduced pressure until a water content of 20–25% by mass, and the above water-miscible organic solvent is added to the concentrated solution, and the honey-like cetirizine dihydrochloride is recrystallized.

A further possibility is that—after the hydrolysis and adjustment of the pH value to 3.8–4.0—the solution of cetirizine base in dichloromethane is extracted with preferably 5–30% hydrochloric acid, the aqueous solution is concentrated under reduced pressure to reduce the water content to 20–25% by mass and then the procedure described above is followed to obtain cetirizine dihydrochloride.

The honey-like residue obtained after the evaporation of the solution of cetirizine base in dichloromethane can be dissolved in a water-miscible organic solvent, preferably acetone, methyl ethyl ketone or tetrahydrofuran, and then the thus-obtained solution of the cetirizine base in the organic solvent is treated with the hydrochloric acid. The acidic solution is worked up by any of the procedure described above to obtain cetirizine dihydrochloride.

According to a further preferred method of the invention, the hydrolysis of the acetic amide of the formula II is carried out with an aqueous solution of an inorganic acid, preferably hydrochloric acid or sulfuric acid at 40–110° C., preferably 70–110° C., suitably at the boiling point of the solution. In general, a 2–25% by mass, preferably 10–20% by mass, suitably about 15% by mass solution of the inorganic acid is employed. To separate the product, the acidic hydrolysate obtained is diluted with water, the pH is adjusted to a value of 3.8–4.0 by the addition of aqueous sodium hydroxide solution, and then the procedure described in connection with the alkaline hydrolysis is followed.

Either the alkaline or the acidic hydrolysis can be performed in the presence of a phase transfer catalyst, and, if desired, also a cosolvent. As the phase transfer catalyst a tetraalkyl-ammonium halide, preferably tetrabutylammonium chloride, triethylbenzylammonium chloride or trioctylmethylammonium chloride (Aliquat 336) or a crown ether, preferably 15-crown-5 or 18-crown-6 can be used. The cosolvent can be an organic solvent being miscible with water such as ethanol, butanol, ethylene glycol or dioxane.

If, in the process of the invention, an acid addition salt of the acetamide of the formula II prepared with an organic acid is used as the starting compound, this organic acid crystallizes from the reaction mixture after the precipitation of the product with an acid. In this case the precipitated organic acid can be separated by filtration before the extraction of the product with dichloromethane to achieve an easier separation of the phases. However, the reaction mixture can be worked up without the separation of the organic acid, too.

Thus, the process of the invention is economical, can be easily carried out and provides cetirizine or the acid addition salt thereof in a very pure form.

A second aspect of the invention refers to the novel intermediates of the formula II, wherein $R_1$ and $R_2$ are as defined above, and acid addition salts thereof formed with inorganic or organic acids. The invention includes the isomers of the {2-[4-(α-phenyl-p-chlorobenzyl)piperazin-1-yl]ethoxy}-acetamides of the formula II and mixtures thereof.

In formula II, in the definition of $R_1$ and $R_2$, the $C_{1-4}$ alkyl group optionally substituted by a phenyl group may have a straight or branched chain such as a methyl, ethyl, isopropyl, tert-butyl or benzyl group etc. The $C_{2-4}$ alkenyl group is, for example, an allyl or a methallyl group.

Preferred compound of the formula II is (RS)-N,N-dimethyl-{2-[4-(α-phenyl-p-chlorobenzyl)piperazin-1-yl]ethoxy}acetamide.

The {2-[4-(α-phenyl-p-chlorobenzyl)piperazin-1-yl]ethoxy}-acetamide of the formula II is prepared by reacting the alkali metal salt of the {2-[4-(α-phenyl-p-chlorobenzyl)piperazin-1-yl]}ethanol of the formula III with a 2-haloacetamide of the formula IV, wherein $R_1$ and $R_2$ are as defined in connection with formula II, X stands for a halo atom, preferably a chloro atom, in an organic aprotic solvent, and, if desired, converting the obtained base of the formula II to an acid addition salt with an inorganic or organic acid or liberating the base from the acid addition salt thereof.

The reaction is carried out at a reaction temperature that is not higher than 120° C., preferably at 60–90° C.

The alkali metal salt of the {2-[4-(α-phenyl-p-chlorobenzyl)-piperazin-1-yl]}ethanol of the formula III is prepared in an indifferent aprotic solvent using an alkali metal hydride, amide or alcoholate, preferably sodium hydride, sodium amide or sodium methylate. The indifferent aprotic solvent is an organic aprotic solvent being indifferent from the point of view of the reaction, preferably benzene, toluene, xylene or N,N-dimethyl-formamide.

The novel {2-[4-(α-phenyl-p-chlorobenzyl)piperazin-1-yl]-ethoxy}-acetamides of the formula II are separated from the reaction mixture in a manner known per se. According to a preferred method, the compound of the formula II is subjected to distribution between water and a water-immiscible organic solvent, the phases are separated, and the organic phase containing the compound of the formula II is evaporated.

According to an especially preferred method of separation, during the above distribution of the compound of the formula II between water and a water-immiscible organic solvent the contaminants are removed from the organic solution by adjusting the pH to a value of 6.2–6.7, preferably about 6.4 with an aqueous solution of an inorganic or organic acid, preferably hydrochloric acid, performing the extraction and separating the phases. Then a further portion of water is added to the organic solution, the pH is adjusted to about 4 by the addition of the aqueous acid, thus, converting the product to the acid addition salt thereof that is dissolved in the aqueous phase. After the separation of the phases, the base is liberated with an alkali, preferably an aqueous sodium hydroxide solution and extracted again with a water-immiscible organic solvent, preferably dichloromethane. After the evaporation of the solution, the residue is dissolved in a lower alkanol, preferably isopropanol, and the solution obtained is treated with an alkanol containing hydrogen chloride, preferably isopropanol containing hydrogen chloride to obtain the dihydrochloride that is precipitated in crystalline form by the addition of a solvent that does not dissolve the product, preferably a di(lower alkyl) ketone, suitably acetone.

According to another preferred separation method of the dihydrochloride of the acetamide of the formula II, after the evaporation of the solution of the base in an organic solvent, the residue is dissolved in cold hydrochloric acid, the water is distilled off under reduced pressure, and, to the residue, a di(lower alkyl) ketone, preferably acetone is added to crystallize the dihydrochloride.

Thus, the acetamide of the formula II is obtained in a very pure form that is suitable for the preparation of pure cetirizine.

The (2-[4-(α-phenyl-p-chlorobenzyl)piperazin-1-yl]}ethanol of the formula III used as the starting compound for the preparation of the acetamide of the formula II has been known in the literature for a long time [H. Morren et al., Belg. Chem. Industrie, XIX, 1176–1185 (1954), Chem. Abstr., 53, 2240e (1959)]. For the preparation of very pure cetirizine it is especially preferred to use {2-[4-(α-phenyl-p-chlorobenzyl)-piperazin-1-yl]}ethanol dihydrochloride monohydrate [m.p.: 196–205° C. (under decomposition), water content (according to Karl Fischer): 4.6%].

The 2-haloacetamides of the formula IV are also known from the literature [W. E. Weaver and W. M. Whaley, J. Amer. Chem. Soc., 69, 516 (1947); J. Kasprzyk et al., J. Heterocycl. Chem., 30, 119 (1993)] and can be easily prepared by the method described in the above references, respectively.

The invention is further elucidated by the following Examples:

Preparation of the {2-[4-(α-phenyl-p-chloro-benzyl)-piperazin-1-yl]ethoxy}acetamides of the formula II

EXAMPLE 1

(RS)-N,N-Dimethyl-{2-[4-(α-phenyl-p-chloro-benzyl)piperazin-1-yl]ethoxy}-acetamide dihydrochloride To a solution of 99.3 g (0.3 moles) of (RS)-{2-[4-(α-phenyl-p-chloro-benzyl)piperazin-1-yl]}ethanol in 500 ml of toluene, 25.8 g (0.33 moles) of 50% sodium amide suspension in toluene are added at 25° C. under nitrogen stream. The reaction mixture is placed into an oil bath heated to 105° C. and reacted for 3 hours. During the reaction, the inner temperature of the reaction mixture remains 80–85° C. Then the reaction mixture is cooled to 40° C., 40.1 g (0.33 moles) of N,N-dimethyl-2-chloro-acetamide are added to it, drop by drop, and stirred at 50° C. for further 2 hours. 120 g of crushed ice are added to the reaction mixture, and the pH is adjusted to 6.4 by the addition of 8 ml of concentrated hydrochloric acid. The phases are separated, 150 ml of water are added to the toluene phase, and the pH of the mixture is adjusted to 4 by the addition of about 21 ml of concentrated hydrochloric acid. The aqueous phase is separated, 300 ml of dichloromethane are added to it, and the pH is adjusted to a value between 7–8 by the addition of about 28 ml (0.28 moles) of 40% aqueous sodium hydroxide solution. The organic phase is separated, extracted with 40 ml of saturated aqueous sodium chloride solution, dried over anhydrous magnesium sulfate, filtered and evaporated under reduced pressure. The honey-like residue (124 g, 99%) is dissolved in 50 ml of isopropanol, and, to the solution obtained, 90 ml of isopropanol containing 25% by mass of hydrogen chloride are added, drop by drop, at room temperature under stirring. To the reaction mixture, 1000 ml of acetone are added under vigorous stirring, and the mixture is stirred for a further hour. The precipitated crystals are filtered, washed 3 times using 50 ml of acetone each time, then with 100 ml of diisopropyl ether.

Thus, 120 g (81.8%) of (RS)-N,N-dimethyl-{2-[4-(α-phenyl-p-chloro-benzyl)piperazin-1-yl]ethoxy}-acetamide dihydro-chloride are obtained, m.p.: 182–190° C.

The spectral data of the base:

ir (KBr): ν C=O 1658 cm$^{-1}$.

pmr (CDCl$_3$): δ ppm 2.41 (bs, 4H, piperazine 3,5-NCH$_2$), 2.53 (t, J=5.8 Hz, 4H, piperazine 2,6-NCH$_2$), 2.62 (t, J=7.0 Hz, 2H, ethoxy NCH$_2$), 2.92 and 2.98 (double s, 2×3H, NCH$_3$), 3.63 (t, J=7.0 Hz, 2H, ethoxy OCH$_2$), 4.14 (s, 2H, COCH$_2$), 4.20 (s, 1H, CH), 7.15–7.37 (m, 9H, ArH).

EXAMPLE 2

(RS)-N,N-Dimethyl-{2-[4-(α-phenyl-p-chloro-benzyl)piperazin-1-yl]ethoxy}-acetamide dihydrochloride The procedure described in Example 1 is followed with the difference that the honey-like residue of the base is dissolved in 100 ml of 20% hydrochloric acid, the solution obtained is concentrated at 10–20° C. under reduced pressure until the water content is reduced to about 5%, the residue is dissolved in 100 ml of isopropanol, to the solution obtained, 1000 ml of acetone are added, and again the procedure of Example 1 is followed. Thus, 110 g=76.4%) of the title compound are obtained, m.p.. 184–189° C.

EXAMPLE 3

(RS)-N,N-Dimethyl-{2-[4-(α-phenyl-p-chloro-benzyl)piperazin-1-yl]ethoxy}-acetamide dihydrochloride The procedure described in Example 1 is followed with the difference that the honey-like residue is dissolved in 30 ml of methanol, and, to the solution obtained, 80 ml of methanol containing 27% of hydrogen chloride are added, then the dihydrochloride is separated as described in Example 1. Thus, 108.9 g (75.6%) of the title compound are obtained, m.p.: 185–190° C.

EXAMPLE 4

(RS)-N,N-Dimethyl-{2-[4-(α-phenyl-p-chloro-benzyl)piperazin-1-yl]ethoxy}-acetamide dihydrochloride 126.8 g (0.3 moles) of (RS)-{2-[4-(α-phenyl-p-chloro-benzyl)-piperazin-1-yl]}ethanol dihydrochloride monohydrate are dissolved in 300 ml of water, and, to the solution obtained, 100 g of crushed ice are added. To the solution obtained, 200 ml of toluene are added, and the pH is adjusted to 8 by the addition of about 60 ml of 40% by mass aqueous sodium hydroxide solution. The phases are separated, the aqueous phase is extracted with 50 ml of toluene. The combined toluene solutions are washed with 50 ml of saturated aqueous sodium chloride solution, dried over anhydrous magnesium sulfate, filtered, then the procedure described in Example 1 is followed.

Thus, 129.2 g (88.1%) of the title compound are obtained, m.p.: 185–190° C. Purity: above 99.6% as determined by HPLC.

EXAMPLE 5

(RS)-N,N-Dimethyl-{2-[4-(α-phenyl-p-chloro-benzyl)piperazin-1-yl]ethoxy}-acetamide fumarate The procedure of Example 1 is followed with the difference that the reaction is carried out on a scale of 0.025 moles, the honey-like base (10.3 g, 98%) is dissolved in 10 ml of iso-propanol, to the solution obtained, 2.9 g (0.024 moles) of fumaric acid are added, and the mixture is heated until dissolution. To the warm solution, 40 ml of ethyl acetate are added and the product is allowed to crystallize. After cooling, the crystals are filtered, and washed with ethyl acetate. Thus, 11.2 g (84.0%) of the title compound are obtained, m.p.: 138–141° C.

EXAMPLE 6

(RS)-N,N-Diethyl-{2-[4-(α-phenyl-p-chloro-benzyl)piperazin-1-yl]ethoxy}-acetamide The procedure described in Example 1 is followed with the difference that the reaction is performed on a scale of 0.025 moles, and, instead of N,N-dimethyl-2-chloroacetamide, 4.11 g (0.0275 moles) of N,N-diethyl-2-chloroacetamide are used. In working up the reaction mixture, the honey-like base (9.98 g, 89.9%) is not converted to the dihydrochloride, but purified by chromatography on a silica gel column that is eluted with chloroform containing 1–10% of methanol by continuously enhancing the polarity of the mixture.

Thus, 9.16 g (82.5%) of the title compound are obtained as a pale yellow honey-like product. $R_f$=0.45 (Kieselgel Merck plate, chloroform:methanol=9:1).

ir (Kbr): ν C=O 1646 cm$^{-1}$.

pmr (CDCl$_3$): δ ppm 1.10 and 1.15 (double t, J=7.0 Hz, 2×3H, CH$_3$), 2.42 (bs, 4H, piperazine 3,5-NCH$_2$), 2.54 (bs, 4H, piperazine 2,6-NCH$_2$), 3.30 and 3.33 (double m, 2×2H, ethyl NCH$_2$), 3.65 (t, J=5.9 Hz, 2H, ethoxy OCH$_2$), 4.14 (s, 2H, COCH$_2$), 4.20 (s, 1H, CH), 7.17–7.37 (m, 9H, ArH).

EXAMPLE 7

(RS)-N,N-Diallyl-{2-[4-(α-phenyl-p-chloro-benzyl) piperazin-1-yl]ethoxy}-acetamide The procedure of Example 3 is followed with the difference that, instead of the N,N-diethyl-2-chloroacetamide, 4.77 g (0.0275 moles) of N,N-diallyl-2-chloroacetamide are employed. The honey-like base (10.5 g, 89%) obtained at the end of working up the reaction mixture is purified by chromatography on a silica gel column using a mixture of chloroform and 2% of methanol as the eluent. Thus, 9.45 g (80.1%) of the title compound are obtained as a pale yellow honey-like product. $R_f$=0.5 (Kieselgel Merck plate, chloroform:methanol=9:1).

ir (KBr): ν C=O 1657 cm$^{-1}$.

pmr (CDCl$_3$): δ 2.42 (bs, 4H, piperazine 3,5-NCH$_2$), 2.53 (bs, 4H, piperazine 2,6-NCH$_2$), 2.62 (t, J=5.8 Hz), 2H, ethoxy NCH$_2$), 3.65 (t, J=5.8 Hz, 2H, ethoxy OCH$_2$), 3.86 (t, J=5.8 Hz), 2H, NCH$_2$), 3.96 (t, J=5.8 Hz), 2H, NCH$_2$), 4.15 (s, 2H, COCH$_2$), 4.20 (s, 1H, CH), 5.16 (m, 4H, CCH$_2$), 5.72 (m, 2H, CH), 7.17–7.38 (m, 9H, ArH).

EXAMPLE 8

(RS)-{2-[4-(α-phenyl-p-chloro-benzyl)piperazin-1-yl]ethoxy}-acetyl morpholide

The procedure described in Example 1 is followed with the difference that the reaction is performed on a scale of 0.05 moles, and, instead of the N,N-dimethyl-2-chloroacetamide, 8.9 g (0.05 moles) of chloroacetyl morpholide are used. The honey-like base (10.4 g, 45.4%) obtained at the end of working up the reaction mixture is purified by chromatography on a silica gel column using a mixture of ethyl acetate and 10% of methanol as the eluent.

Thus, 8.3 g (36.2%) of the title compound are obtained as an oily product. $R_f$=0.35 (Kieselgel Merck plate, chloroform:methanol=9:1).

ir (KBr): ν C=O 1655 cm$^{-1}$.

pmr (CDCl$_3$): δ 2.41 (bs, 4H, piperazine 3,5-NCH$_2$), 2.53 (bs, 4H, piperazine 2,6-NCH$_2$), 2.61 (t, J=5.6 Hz, 2H, ethoxy NCH$_2$), 3.50 (m, 4H, morpholino NCH$_2$), 3.57 (m, 4H, morpholino OCH$_2$), 3.62 (t, J=5.6 Hz, 2H, ethoxy OCH$_2$), 4.13 (s, 2H, COCH$_2$), 4.20 (s, 1H, CH), 7.16–7.36 (m, 9H, ArH).

ms (Cl): (M+1)$^+$=458.

EXAMPLE 9

(RS)-N,N-Dicyclohexyl-{2-[4-(α-phenyl-p-chloro-benzyl)-piperazin-1-yl]ethoxy}-acetamide The procedure described in Example 1 is followed with the difference that the reaction is carried out on a scale of 0.02 moles, and, instead of the N,N-dimethyl-2-chloroacetamide, 5.2 g (0.02 moles) of N,N-dicyclohexyl-2-chloroacetamide is used. Thus, 9.8 g, (88.9%) of the title compound are obtained as an honey-like product. Purity: 99% as determined by HPLC.

ir (KBr): ν C=O 1656 cm$^{-1}$.

pmr (CDCl$_3$): δ 1.23 (m, 4H, cyclohexyl 4-CH$_2$), 1.46–1.78 (m, 16H, cyclohexyl 2,3,5,6-CH$_2$), 2.45 (bs, 4H, piperazine 3,5-NCH$_2$), 2.59 (bs, 4H, piperazine 2,6-NCH$_2$), 2.67 (m, 2H, ethoxy NCH$_2$), 3.48 (m, 2H, cyclohexyl CH), 3.67 (m, 2H, ethoxy OCH$_2$), 4.08 (s, 2H, COCH$_2$), 4.21 (s, 1H, CH), 7.17–7.36 (m, 9H, ArH).

EXAMPLE 10

(RS)-N,N-Dicyclohexyl-{2-[4-(α-phenyl-p-chloro-benzyl)piperazin-1-yl]ethoxy}-acetamide dimaleinate 1.1 g of the honey-like base obtained as described in Example 9 are dissolved in 3 ml of isopropanol, to the solution obtained, a solution of 0.23 g of maleic acid in 2 ml of isopropanol are added at room temperature, and the reaction mixture is stirred at room temperature for 14 hours. The crystals precipitated are filtered, and washed with some isopropanol.

Thus, 0.81 g (60.8 l) of the title product are obtained, m.p.: 149–152° C. Purity: 99.6% as determined by HPLC.

EXAMPLE 11

(RS)-N,N-Dibenzyl-{2-[4-(α-phenyl-p-chloro-benzyl)piperazin-1-yl]ethoxy}-acetamide The procedure described in Example 1 is followed with the exception that the reaction is performed on a scale of 0.05 moles, and, instead of the N,N-dimethyl-2-chloroacetamide, 13.7 g (0.05 moles) of N,N-dibenzyl-2-chloroacetamide are used. The honey-like base (25.1 g, 88.5%) obtained at the end of working up the reaction mixture is purified by chromatography on a silica gel column that is eluted with mixtures of ethyl acetate and n-hexane by continuously enhancing the polarity of the mixture. Thus, 17.0 g (57%) of the title compound are obtained as a honey-like product. R$_f$=0.7 (Kieselgel Merck plate, ethyl acetate:methanol=1:1).

ir (KBr): ν C=O 1654 cm$^{-1}$.

pmr (CDCl$_3$): δ 2.35 (bs, 4H, piperazine 3,5-NCH$_2$), 2.49 (bs, 4H, piperazine 2,6-NCH$_2$), 2.59 (t, J=5.5 Hz, 2H, ethoxy NCH$_2$), 3.68 (t, J=5.5 Hz, 2H, ethoxy OCH$_2$), 4.16 (s, 1H, CH), 4.25 (s, 2H, COCH$_2$), 4.43 (s, 2H, PhCH$_2$), 4.55 (s, 2H, PhCH$_2$), 7.16–7.37 (m, 9H, ArH).

EXAMPLE 12

(RS)-N,N-Dimethyl-{2-[4-(α-phenyl-p-chloro-benzyl)piperazin-1-yl]ethoxy}-acetamide dihydrochloride To a solution of 99.3 g (0.3 moles) of (RS)-{2-[4-(α-phenyl-p-chloro-benzyl)piperazin-1-yl]}ethanol in 500 ml of toluene, 17.8 g (0.33 moles) of sodium methylate are added at 25° C. under vigorous stirring and nitrogen stream. The reaction mixture is heated to boiling and 200 ml of solvent are distilled off, then 500 ml of absolute toluene are added at the same rate as the distillation proceeds, thus, maintaining the volume of the reaction mixture between 250–350 ml. At the end of the addition of the toluene, no methanol can be detected in the distillate. Heating of the reaction mixture is stopped, 200 ml of absolute toluene are added, the temperature of the mixture is adjusted to 40° C. and 40.1 g (0.33 moles) of N,N-dimethyl-2-chloroacetamide are added, drop by drop, and the reaction mixture is stirred at 50° C. for further 2 hours. The reaction mixture is worked up as described in Example 1.

Thus, 120 g (81.8%) of (RS)-N,N-dimethyl-{2-[4-(α-phenyl-p-chloro-benzyl)piperazin-1-yl]ethoxy}-acetamide dihydrochloride are obtained the purity of which is identical with that of the product of Example 1.

Preparation of the {2-[4-(α-phenyl-p-chlorobenzyl)-piperazin-1-yl]ethoxy}acetic acid of the formula I

EXAMPLE 13

(RS)-{2-[4-(α-phenyl-p-chlorobenzyl)-piperazin-1-yl]ethoxy}-acetic acid dihydrochloride To a solution of 97.8 g (0.2 moles) of (RS)-N,N-dimethyl-{2-[4-(α-phenyl-p-chloro-benzyl)piperazin-1-yl]ethoxy}-acetamide dihydrochloride in 340 ml of water, a solution of 80 g (2.0 moles) of sodium hydroxide in 200 ml of water is added under stirring, and the suspension is boiled for 2.5 hours while nitrogen stream is bubbled through it. The reaction mixture is allowed to cool to 40° C., diluted with 500 ml of water, made acidic until a pH of 3.8 by the addition of 120 ml of concentrated hydrochloric acid, and extracted with 400 ml of dichloromethane, then with 200 ml of dichloromethane. The combined organic phases are evaporated under reduced pressure, the residue is dissolved in 50 ml of water, acidified by the addition of 24 ml of concentrated hydrochloric acid, and evaporated to dryness under reduced pressure. The thick oily residue is dissolved in 50 ml of acetone, to the solution obtained further 550 ml of acetone are added, and the mixture is stirred for 1 hour. The precipitated crystalline product is filtered, washed with acetone, then with diethyl ether, and dried under reduced pressure.

Thus, 74.3 g (80.5%) of the pure title compound are obtained, m.p.: 226–228° C. The purity of the product corresponds to the quality requirements given in Eur. Pharm., 3, 1997, 1084.

EXAMPLE 14

(RS)-{2-[4-(α-phenyl-p-chlorobenzyl)-piperazin-1-yl]ethoxy}-acetic acid dihydrochloride The procedure described in Example 13 is followed with the difference that, instead of the (RS)-N,N-dimethyl-{2-[4-(α-phenyl-p-chloro-benzyl)piperazin-1-yl]ethoxy}-acetamide dihydrochloride, 83.2 g (0.2 moles) of (RS)-N,N-dimethyl-{2-[4-(α-phenyl-p-chloro-benzyl)piperazin-1-yl]ethoxy}-acetamide base are used. Thus, 75.0 g (81.3%) of the title compound are obtained, m.p. 225–228° C. The purity of the product corresponds to the quality requirements given in Eur. Pharm., 3, 1997, 1084.

EXAMPLE 15

(RS)-{2-[4-(α-phenyl-p-chlorobenzyl)-piperazin-1-yl]ethoxy}-acetic acid dihydrochloride The procedure described in Example 13 is followed with the difference that, instead of the (RS)-N,N-dimethyl-{2-[4-(α-phenyl-p-chloro-benzyl)piperazin-1-yl]ethoxy}-acetamide dihydrochloride, 106.4 g (0.2 moles) of (RS)-N,N-dimethyl-{2-[4-(α-phenyl-p-chloro-benzyl)piperazin-1-

EXAMPLE 16

(RS)-{2-[4-(α-phenyl-p-chlorobenzyl)-piperazin-1-yl]ethoxy}-acetic acid dihydrochloride The procedure described in Example 14 is followed with the difference that, instead of the (RS)-N,N-dimethyl-{2-[4-(α-phenyl-p-chloro-benzyl)piperazin-1-yl]ethoxy}-acetamide, 104.4 g (0.2 moles) of (RS)-N,N-diethyl-{2-[4-(α-phenyl-p-chloro-benzyl)piperazin-1-yl]ethoxy}-acetamide are used, 100 ml of dioxane are employed as cosolvent, and, during the alkaline hydrolysis, the reaction mixture is boiled for 4 hours. Thus, 69.1 g (74.9%) of the title compound are obtained, m.p.: 225–228° C. The purity of the product corresponds to the quality requirements given in Eur. Pharm., 3, 1997, 1084.

EXAMPLE 17

(RS)-{2-[4-(α-phenyl-p-chlorobenzyl)-piperazin-1-yl]ethoxy}-acetic acid dihydrochloride The procedure described in Example 14 is followed with the difference that, instead of the (RS)-N,N-dimethyl-{2-[4-(α-phenyl-p-chloro-benzyl)piperazin-1-yl]ethoxy}-acetamide, 110.0 g (0.2 moles) of (RS)-N,N-diallyl-{2-[4-(α-phenyl-p-chloro-benzyl)piperazin-1-yl]ethoxy}-acetamide are used, 100 ml of dioxane are employed as cosolvent, and, during the alkaline hydrolysis, the reaction mixture is boiled for 10 hours Thus, 64.0 g (69.3%) of the title compound are obtained, m.p.: 225–228° C. The purity of the product corresponds to the quality requirements given in Eur. Pharm., 3, 1997, 1084.

EXAMPLE 18

(RS)-{2-[4-(α-phenyl-p-chlorobenzyl)-piperazin-1-yl]ethoxy}-acetic acid dihydrochloride The procedure described in Example 14 is followed with the difference that, instead of the (RS)-N,N-dimethyl-{2-[4-(α-phenyl-p-chloro-benzyl)piperazin-1-yl]ethoxy}-acetamide, 107.7 g (0.2 moles) of (RS)-{2-[4-(α-phenyl-p-chlorobenzyl)-piperazin-1-yl]ethoxy}-acetyl morpholide are used, and the hydrolysis is carried out for 5 hours under boiling. Thus, 72.4 g (78.4%) of the title compound are obtained, m.p.: 225–228° C. The purity of the product corresponds to the quality requirements given in Eur. Pharm., 3, 1997, 1084.

EXAMPLE 19

(RS)-{2-[4-(α-phenyl-p-chlorobenzyl)-piperazin-1-yl]ethoxy}-acetic acid dihydrochloride The procedure described in Example 13 is followed with the difference that, after the hydrolysis, the reaction mixture is diluted with 3500 ml of water, extracted with 600 ml of ethyl acetate and 200 ml of diisopropyl ether, the residues of the organic solvents are removed from the aqueous solution under reduced pressure, and the procedure of Example 13 is continued. Thus, 68.1 g (73.8%) of the title compound are obtained, m.p.: 226–228° C. The purity of the product corresponds to the quality requirements given in Eur. Pharm., 3, 1997, 1084.

EXAMPLE 20

(RS)-{2-[4-(α-phenyl-p-chlorobenzyl)-piperazin-1-yl]ethoxy}-acetic acid dihydrochloride The procedure described in Example 13 is followed with the difference that, after the hydrolysis, the reaction mixture is diluted with 3500 ml of water, cooled to 0° C., the precipitated crystalline cetirizine sodium salt is allowed to sediment for 1 hour, filtered, then dissolved in 1000 ml of water, the pH is adjusted to a value of 3.8 by the addition of hydrochloric acid, then the procedure of Example 13 is continued. Thus, 65.7 g (71.2%) of the title compound are obtained. The purity of the product corresponds to the quality requirements given in Eur. Pharm., 3, 1997, 1084.

EXAMPLE 21

(RS)-{2-[4-(α-phenyl-p-chlorobenzyl)-piperazin-1-yl]ethoxy}-acetic acid dihydrochloride The procedure described in Example 13 is followed with the difference that the hydrolysis is carried out with 170 ml (2.0 moles) of concentrated hydrochloric acid, and, at the end of the hydrolysis, the pH of the reaction mixture is adjusted to the desired value of 3.8 with about 270 ml of 40% aqueous sodium hydroxide solution. Thus, 70.6 g (76.5%) of the title compound are obtained, m.p.: 225–228° C. The purity of the product corresponds to the quality requirements given in Eur. Pharm., 3, 1997, 1084.

EXAMPLE 22

(RS)-{2-[4-(α-phenyl-p-chlorobenzyl)-piperazin-1-yl]ethoxy}-acetic acid dihydrochloride The procedure described in Example 13 is followed with the difference that the hydrolysis is carried out with 170 ml (0.9 moles) of 50% sulfuric acid, and, at the end of the hydrolysis, the pH of the reaction mixture is adjusted to the desired value of 3.8 with about 260 ml of 40% aqueous sodium hydroxide solution. Thus, 67.3 g (72.9%) of the title compound are obtained, m.p.: 225–228° C. The purity of the product corresponds to the quality requirements given in Eur. Pharm., 3, 1997, 1084.

EXAMPLE 23

(RS)-{2-[4-(α-phenyl-p-chlorobenzyl)-piperazin-1-yl]ethoxy}-acetic acid dihydrochloride The procedure described in Example 13 is followed with the difference that, in addition to the aqueous sodium hydroxide solution, also 2 g of Aliquat 336 (trioctylmethyl ammonium chloride) are added to the reaction mixture. Thus, 74.9 g (81.2%) of the title compound are obtained, m.p.: 226–228° C. The purity of the product corresponds to the quality requirements given in Eur. Pharm., 3, 1997, 1084.

EXAMPLE 24

(RS)-{2-[4-(α-phenyl-p-chlorobenzyl)-piperazin-1-yl]ethoxy}-acetic acid dihydrochloride The procedure described in Example 13 is followed with the difference that, in addition to the aqueous sodium hydroxide solution, also 1 g of 15-crown-5 (1,4,7,10,13-pentaoxacyclo-pentadecane) is added to the reaction mixture. Thus, 76.1 g (82.5%) of the title compound are obtained, m.p.: 226–228° C. The purity of the product corresponds to the quality requirements given in Eur. Pharm., 3, 1997, 1084.

EXAMPLE 25

(RS)-{2-[4-(α-phenyl-p-chlorobenzyl)-piperazin-1-yl]ethoxy}-acetic acid dihydrochloride The procedure described in Example 13 is followed with the difference that the hydrolysis is carried out with 280 ml of 40% aqueous potassium hydroxide solution. Thus, 75.0 g (81.3%) of the title compound are obtained, m.p.: 226–228° C. The purity of the product corresponds to the quality requirements given in Eur. Pharm., 3, 1997, 1084.

What is claimed is:

1. A process for the preparation of a compound of the Formula (II)

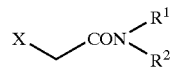

wherein $R_1$ and $R_2$ are each independently a $C_1$ to $C_4$ alkyl group optionally substituted by a phenyl group, a $C_2$ to $C_4$ alkenyl group, or a cyclohexyl group, or $R_1$ and $R_2$ form together with the adjacent nitrogen atom, a morpholino group, or a pharmaceutically acceptable acid addition salt thereof, which comprises the step of reacting an alkali metal salt of a compound of the Formula (III)

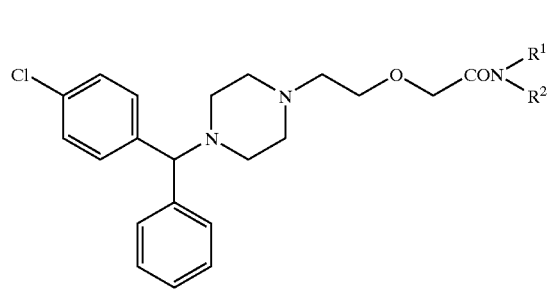

with a compound of the Formula (IV)

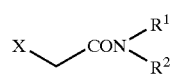

wherein $R_1$ and $R_2$ are as defined above and is a halo atom, and where the pharmaceutically acceptable acid addition salt of the Formula (II) is to be obtained, converting the compound of the Formula (II) to the pharmaceutically acceptable acid addition salt with an inorganic or organic acid.

2. The process defined in claim 1 wherein in the compound of the Formula (IV) X is chloro.

3. A process for preparing a compound of the Formula (I)

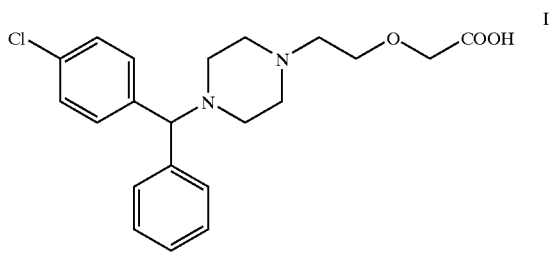

or a pharmaceutically acceptable acid addition or metal salt thereof, which comprises the steps of:

(a) reacting an alkali metal salt of a compound of the Formula (III)

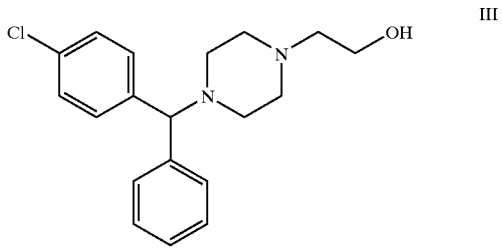

with a compound of the Formula (IV)

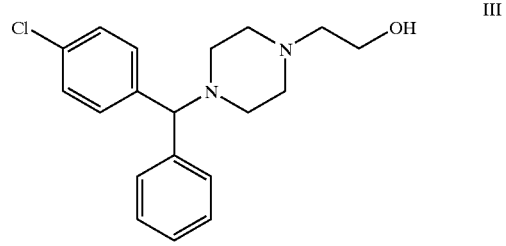

wherein $R_1$ and $R_2$ are each independently a $C_1$ to $C_4$ alkyl group optionally substituted by a phenyl group, $C_2$ to $C_4$ alkenyl group, or a cyclohexyl group, or $R_1$ and $R_2$ form together with the adjacent nitrogen atom, a morpholino group and X is a halo atom to obtain a compound of the Formula (II)

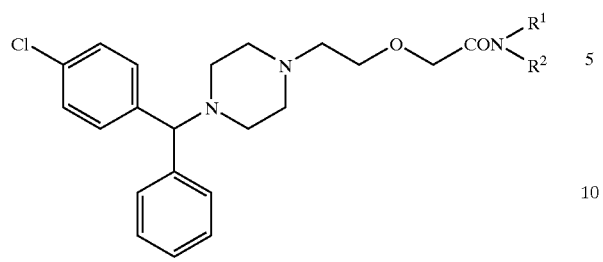

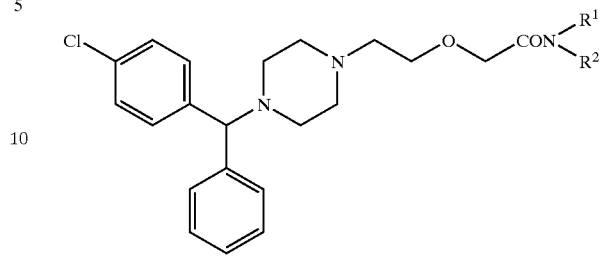

wherein $R_1$ and $R_2$ are as defined above, and where the pharmaceutically acceptable acid addition salt of the Formula (II) is to be obtained, converting the compound of the Formula (II) to the pharmaceutically acceptable acid addition salt with an inorganic or organic acid; and (b) hydrolyzing in an acidic or basic medium the compound of the Formula (II)

or a pharmaceutically acceptable acid addition salt thereof at 40 to 110° C. for 1 to 8 hours to obtain the desired compound.

* * * * *